United States Patent
Gill

[11] Patent Number: 6,090,073
[45] Date of Patent: Jul. 18, 2000

[54] DIRECT PERCUTANEOUS ENDOSCOPIC JEJUNOSTOMY METHOD AND APPARATUS

[75] Inventor: Inderbir S. Gill, Lexington, Ky.

[73] Assignee: Corpak, Inc., Wheeling, Ill.

[21] Appl. No.: 09/217,488

[22] Filed: Dec. 21, 1998

Related U.S. Application Data

[62] Division of application No. 08/443,149, May 17, 1995, Pat. No. 5,851,195.

[51] Int. Cl.[7] ................................................... A61M 5/178
[52] U.S. Cl. ........................... 604/164; 604/164; 206/363
[58] Field of Search ............................... 604/49–53, 164, 604/165, 175, 280, 264, 167, 184, 185; 128/658, 753, 754, 772, 747, 748, 749, 750, 751; 206/363–365

[56] References Cited

U.S. PATENT DOCUMENTS

| | | | |
|---|---|---|---|
| 4,573,576 | 3/1986 | Krol | 206/471 |
| 4,598,699 | 7/1986 | Garen et al. | 128/4 |
| 4,961,430 | 10/1990 | Sheahon | 128/754 |
| 5,151,086 | 9/1992 | Duh et al. | 604/51 |
| 5,356,382 | 10/1994 | Picha et al. | 604/105 |
| 5,512,037 | 4/1996 | Russell et al. | 600/206 |

*Primary Examiner*—Wynn Wood Coggins
*Assistant Examiner*—Kevin C. Sirmons
*Attorney, Agent, or Firm*—Wallenstein & Wagner, Ltd.

[57] ABSTRACT

A method and apparatus of administering a percutaneous access catheter directly into the jejunum of a patient. The apparatus including a wire having a proximal and distal end. The distal end of the wire includes a probe and the proximal end includes a bend. The needle is provided within a sheath which movably surrounds the wire such that the probe is emergent from the sheath. The method including the steps of administering the sheath and wire of the present invention such that the wire enters the mouth of the patient, passes through the esophagus and extends into the jejunum of the patient, moving the wire to expose the probe beyond the sheath, piercing the wire through the jejunal wall and through the abdominal wall. The method further including attaching a percutaneous access tube to the proximal end of the wire and pulling the wire from its distal end, thereby pulling the tube such that it extends from inside the jejunum to outside the patient's abdominal wall.

5 Claims, 4 Drawing Sheets

DIRECT PERCUTANEOUS ENDOSCOPIC JEJUNOSTOMY METHOD AND APPARATUS

This application is a divisional of application Ser. No. 08/443,149 filed May 17, 1995, issued as U.S. Pat. No. 5,851,195.

DESCRIPTION

1. Technical Field

This invention relates to percutaneous enteral catheters and the medical procedure for intubating such apparatus. The method of the present invention relates to a procedure for intubation of an enteral catheter, other than by initial incision or puncture of the patient's abdomen from the outer surface. More specifically, the present invention, in its preferred embodiment, relates to a catheter apparatus for direct access into the small intestine, preferably into the jejunum, and a procedure for intubation of the same.

2. Background of the Invention

Patients with a loss of an ability to achieve sufficient caloric and nutrition intake may require enteral feeding. Frequently, enteral feeding can be achieved through the use of a percutaneous access catheter, such as a gastrostomy feeding tube. However, in certain situations, such as patients who are prone to aspiration pneumonia, gastroesophageal reflux, or suffer from duodenal obstruction, the patient may require feeding at a point beyond the pyloric valve, namely in the jejunum.

Some previously known techniques for placing a feeding tube into the small intestine generally include: (1) placement of a percutaneous endoscopic gastrostomy (PEG) tube and passing a weighted or non-weighted feeding tube into the duodenum or the jejunum; (2) surgically placing a direct jejunostomy tube; or, (3) placing a tube directly into the jejunum with a known PEG-like procedure, whereby the jejunum is accessed by stab-piercing the jejunum from outside the abdominal wall.

The first of the general techniques identified above results in a gastrostomy tube which, either by extending the gastrostomy tube or by inserting a longer tube through an existing gastrostomy tube, includes a length of tubing within the stomach which may lead into the small intestine. An example of this may be seen in FIG. 1. This technique utilizes known endoscopic procedures for placing a percutaneous gastrostomy tube, and essentially extending the feeding tube within the patient so that the tube may terminate in the jejunum.

A practiced procedure for the placement of such a tube involves the use of a needle catheter (such as a 14-gauge needle catheter) to pierce the abdominal wall, enter the peritoneal cavity, and pierce the stomach wall. According to this procedure, an endoscope is first administered through the patient's mouth, down the esophagus, and into the stomach. Once the needle catheter pierces the stomach wall, a wire is inserted into the stomach, through the needle catheter, and is grasped by a means provided in the working channel of the endoscope (such as an endoscopic forceps or snare). As the endoscope is withdrawn, the wire is pulled out with it, resulting in the wire remaining through the patient's abdomen and out through the patient s mouth. A gastrostomy tube is attached to the wire at the mouth end, and the wire is pulled from the opposite end. An incision is made to allow one end of the gastrostomy tube to pass through a stoma of the stomach wall and the peritoneum and abdomen wall of the patient. The gastrostomy tube usually includes a disc, balloon or similar retention member near the end opposite that which is attached to the wire. The retention member abuts the interior of the stomach wall and assists with retention of the gastrostomy tube. Examples of this method of placing a percutaneous endoscopic gastrostomy (PEG) tube is described in U.S. Pat. Nos. 5,167,627; 5,112,310; and, 4,026,481. In order to access the jejunum, a tube extends from the gastrostomy tube within the stomach so that it may be pulled or pushed into the jejunum with a second pass of the endoscope. This procedure is described in U.S. Pat. No. 4,668,225, entitled "Gastrostomy Tube and Gastrostomy-Jejunal Feeding Tube Combination."

There are a number of problems with the procedure and apparatus described above. First, the jejunal tube placement is not exact, and it is sometimes difficult to situate the distal end of the tube into the jejunum, rather than the tube remaining in the stomach or the duodenum, and potentially being regurgitated into the stomach. Second, duodenal obstruction, or other complications, may block the placement of the distal end of the tube into the jejunum. Third, such tube placement is obviously difficult in situations where it is necessary to have a tube terminating in the stomach and another in the duodenum or jejunum, such as when drainage of the stomach and feeding into the jejunum is desired. Also, the procedure described above requires at least two passes of an endoscope (once to grasp the wire for the gastrostomy tube placement, and again to grasp the end of the tube to attempt placement of the tube end in the jejunum).

The second technique identified above, namely a surgical procedure for administering a direct jejunostomy tube, requires incisions through the abdomen, and an incision through the wall of the jejunum, such that the jejunostomy tube may be placed directly and sutured in place. Alternatively, an incision is made through the abdominal wall, a needle catheter is inserted through the wall of the jejunum, and the jejunostomy tube is inserted through the needle catheter. The jejunostomy tube is then either brought through the abdominal incision and sutured in place, or it is brought through the abdominal wall through a needle catheter as well. In either case, the jejunum is then sutured to the abdominal wall to restrict movement of the jejunum.

There are a number of problems associated with the surgical placement procedures. The most profound drawback of this procedure is that it involves open surgery, requiring a substantially long surgical incisions into the abdomen, followed by sutures. Because such a surgical procedure requires general anesthesia, there is increased complexity in the procedure and the risk of patient morbidity. Further, such a procedure causes discomfort to the patient, is time consuming, and there is an increased risk of infection, particularly with the chance that intestinal contents may contact the skin.

The third technique identified above as a method for placing a jejunal feeding tube essentially involves a slight modification of the same practiced procedure as for placing a PEG tube (i.e., piercing the abdominal wall and enteral organ with a needle catheter, inserting a wire through the catheter, and pulling the wire from the enteral organ to outside the mouth via an endoscope). However, the jejunum is usually in motion (due to peristalsis) and substantially smaller in comparison to the stomach. Therefore, it is difficult for the physician to administer the wire into the jejunum (whether by needle catheter or by an incision). Because of this, the practiced techniques involve essentially stabbing the jejunum from outside the abdominal wall. For example, a procedure for placing a jejunostomy tube is described in an article entitled "Direct Percutaneous Endoscopic Jejunostomies," M. Shike et al., *Gastrointestinal Endoscopy*, 37:62–65 (1991), in which the physician performs a "swift stab" through the abdominal wall and into the jejunum, and a catheter needle is inserted. This method is difficult, technically inexact and risks potential harm to the patient.

Yet another such "stab" procedure for administering a jejunostomy tube is described in U.S. Pat. No. 5,151,086. In this procedure, laparoscopic assistance is used and T-fasteners are inserted into the jejunum to gain a degree of stabilization of the jejunum to the abdominal wall. The abdominal wall and jejunum are then pierced with a needle catheter and, after dilating the jejunostomy, a jejunostomy tube is inserted and secured.

Because of the natural undulating movement of the jejunum, accurate stabbing of the jejunum is made difficult or the possibility exists of stabbing through the opposite wall of the jejunum. Hence, these techniques are very difficult and not reliable. Also, in the event the stab and immediate tube insertion is not achieved, multiple stabs must be made, or an alternative method must be used, likely necessitating open surgical placement. Further, such a situation increases discomfort and risk of infection to the patient, and delays placement of the jejunostomy tube.

In light of the foregoing, there exists a need for a method and device for direct percutaneous enteral jejunostomy without the problems associated with the previously-known methods and devices for catheters of jejunal access.

SUMMARY OF THE INVENTION

The present invention provides a wire for administering a percutaneous enteral tube which includes a proximal end and a distal end separated by a wire body. The distal end of the wire includes a piercing tip, preferably in the form of a needle. The proximal end of the wire includes a bend, preferably a bend which forms a loop. A sheath is provided which movably surrounds at least the piercing tip of the wire, such that the piercing tip is emergent from the sheath.

The present invention also provides a method of administering a percutaneous access catheter directly into the small bowel, preferably the jejunum, of a human or animal body having a mouth, esophagus, stomach and jejunum. The method broadly includes the step of administering an enteroscope and administering a wire having a proximal and a distal end, such that the wire enters the mouth of the body through an enteroscope, passes through the esophagus, and the distal end of the wire is within the small intestine. The distal end of the wire is pierced through the small bowel, preferably the jejunum, from inside the jejunum and it is then pierced through the abdominal wall. The enteroscope is removed, leaving the wire in place. A percutaneous access tube is attached to the proximal end of the wire. The distal end of the wire is pulled, such that the percutaneous access tube is pulled through the esophagus and stomach into the jejunum. The tube is pulled, such that it extends from inside the jejunum to outside the body through the abdominal wall.

In the preferred embodiment, the wire is administered into the body via the working channel of an endoscope, which is intubated through the mouth, esophagus, stomach and into the jejunum of the body. Preferably, the distal end of the wire includes a needle, and a retractable sheath covers at least the distal end of the wire until the wire is pierced through the jejunum and the abdominal wall.

Yet another object of the present invention is to provide a kit assembly for performing the procedure of administering a direct percutaneous enteral jejunostomy tube. The kit assembly includes a wire and a sheath, such as that described above. Preferably, the wire is already strung through the sheath when provided in the kit. The kit also provides other items utilized in the procedure, including a percutaneous enteral tube, preferably with a low-profile retention bumper, and an external fixation device for the tube (for abutment against the skin at the abdomen). The kit may also provide other usefull instruments for the intubation procedure, including hemostats (for clamping the sheath and wire combination together after they are pierced through the abdominal wall), sterilization swabs, an adaptor for connecting the tube to a feeding set, and water-based lubricant.

Other advantages and aspects of the present invention will become apparent upon reading the following description of the drawings and detailed description of the invention.

DETAILED DESCRIPTION

Figure 1:
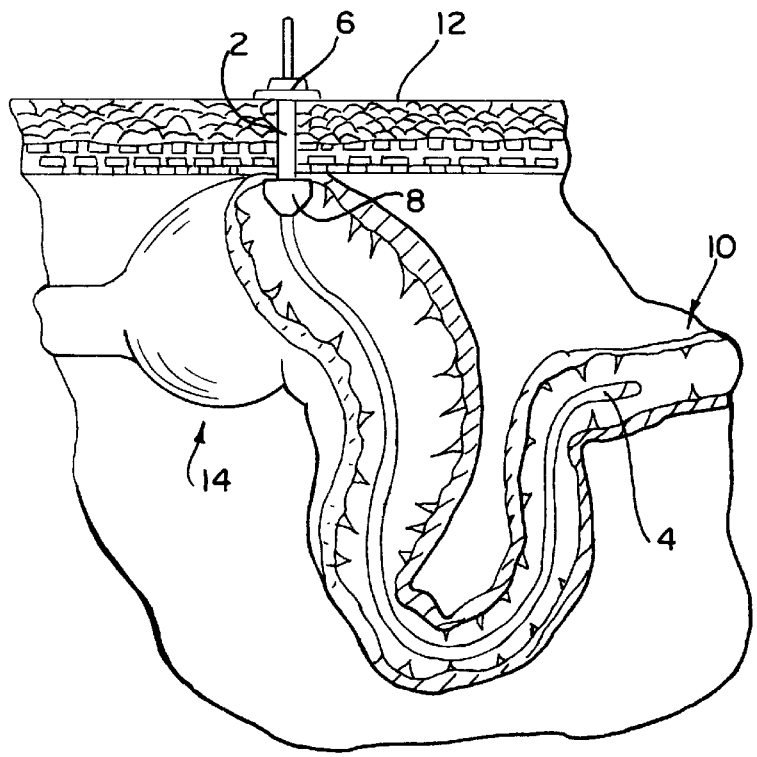
FIG. 1 is a partial cross-section view of a stomach and a prior art percutaneous gastrostomy tube with a jejunal extension.

While this invention is susceptible of embodiment in many different forms, there is shown in the drawings and will herein be described in detail a preferred embodiment of the invention with the understanding that the present disclosure is to be considered as an exemplification of the principles of the invention and is not intended to limit the broad aspect of the invention to the embodiments illustrated.

FIG. 1 discloses a prior art percutaneous endoscopic gastrostomy (PEG) tube 2 with an extension of tubing 4 into the jejunum 10. The PEG tube 2 includes an external fixation device 6 which abuts against the abdominal skin 12 of the human or animal body. The PEG tube 2 also includes a retention bumper 8 which abuts against the interior stomach 14.

Figure 2:
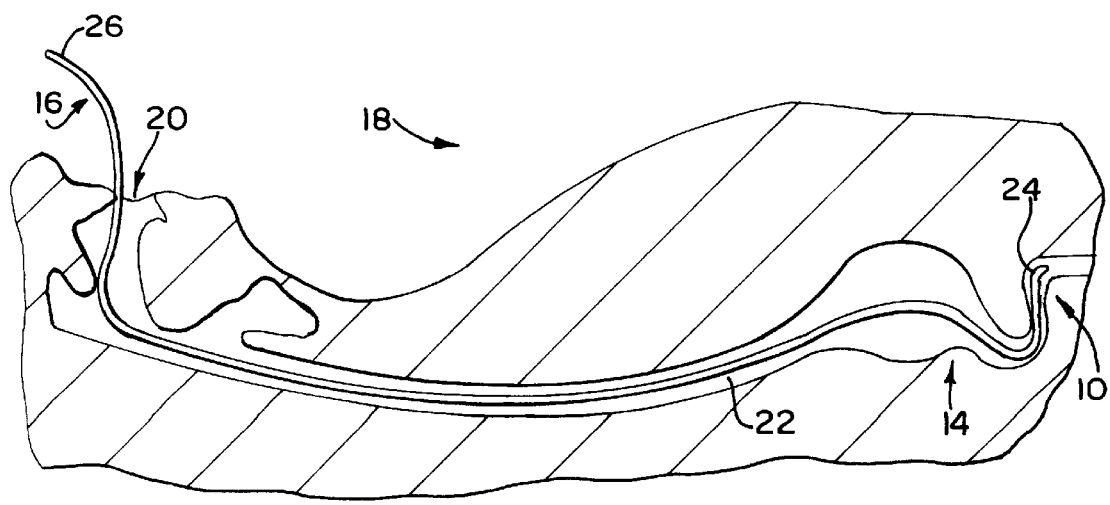
FIG. 2 is a cross-section view demonstrating an endoscope inserted into the body and passed into the jejunum.

FIGS. 2 through 8 disclose a preferred method of the present invention for the intubation of a direct percutaneous endoscopic device into the small bowel of a patient. The Figures depict the preferred embodiment of the present invention, which concerns intubation of a direct percutaneous endoscopic jejunostomy (PEJ) tube. As is best shown in FIG. 2, an endoscope 16 is intubated within the patient's body 18 by passing endoscope 16 through the patient's mouth 20, through the esophagus 22, into the stomach 14 and terminating at a distal end 24 in the small bowel, preferably the jejunum 10. Endoscope 16 is preferably selected as suitable for manipulating into the small intestine, such as a push enteroscope. Endoscope 16 includes a working channel (not shown) which passes from the proximal end 26 to the distal end 24 of the endoscope 16.

A flexible member, such as an elongated wire 28, is provided in the working channel of the endoscope 16, preferably placed within the working channel prior to intubation of the endoscope 16, but also may be passed through the working channel after the endoscope 16 has been intubated into the jejunum 10. The length of the wire 28 is substantially greater than that of a typical needle catheter used for PEG placement. The wire 28 has a length greater than that sufficient for the wire 28 to extend outside the patient's mouth and into the patient's body to the jejunum 10. Preferably, the length of the wire 28 is in the range of 290 to 305 centimeters (115 to 120 inches).

Figure 9:
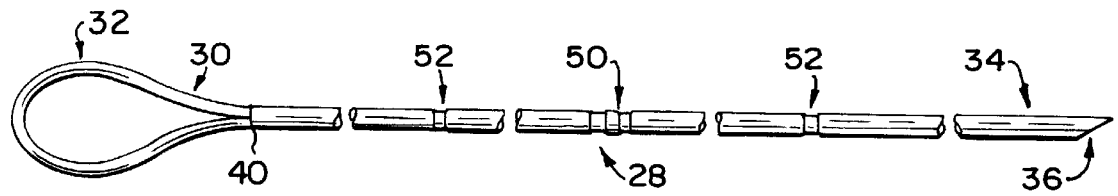
FIG. 9 discloses an embodiment of a wire used in practicing the present invention.

As is best shown in FIG. 9, the wire 28 has a proximal end 30 and a distal end 34. At the distal end 34 of the wire 28 is a piercing tip 36, preferably as a tapered needle point. The proximal end 30 of the wire 28 includes a bend, preferably as a loop 32. It should be noted that the loop 32, as disclosed in FIG. 9, is a continuous bend, or folding back of the wire. However, it should be clear that the loop 32 may be formed as an eyelet, or some other smooth-bodied connector suitable for attaching a catheter tube for intubation in the body 18 by pulling the wire 28 (as described below). In the preferred embodiment, the loop connection 40 is smooth. The body of the loop 32 is also smooth, thereby allowing passage of the proximal end of the wire 28 through the body 18 without significant resistance or snagging.

The wire 28 is preferably semi-rigid, such as a thin cannula, or similar wire with an inner lumen. The outer diameter of the wire should be less than 1 millimeter and preferably approximately 0.80 millimeter (0.032 inch) and the inner lumen of approximately 0.50 millimeter (0.020 inch). Such a wire provides sufficient rigidity and flexibility for performing manipulation of the wire in this procedure, while having an outer diameter which is small enough to easily puncture and pass through the wall of the small bowel and the abdominal wall.

One type of thin cannula is that which is used for biopsy sampling within the body, as is described further in U.S. Pat. No. 4,230,123. The wire 28 of the present invention, however, differs from a cannula, as the present device need not have a continuous inner lumen or have access of the inner lumen at the proximal end 30. Rather, in the preferred embodiment of the present invention, the proximal end 30 of the wire 28 includes a loop 32 which is integrally attached, and preferably continuous, with the proximal end 30 of the wire 28. In the preferred embodiment, therefore, the loop 32 of the wire 28 blocks the inner lumen of the wire 28, yet would provide a smooth surface to minimize snagging or drag when passing through the patient's body, and is therefore greatly different from a biopsy cannula.

Figure 10:
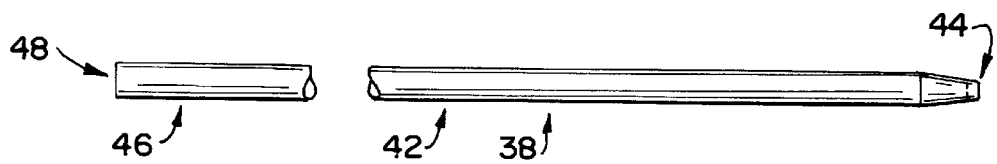
FIG. 10 discloses an embodiment of a sheath used in practicing the present invention; and, FIG. 11 is a side elevation view of a kit having the devices necessary for practicing the present invention.

As disclosed in FIG. 10, a sheath 38 is also provided. The sheath 38 has a sheath body 42, a distal end 44, and a proximal end 46. The sheath 38 includes an inner lumen 48, which passes from the proximal end 46 to the distal end 44, and is suitable for receiving the wire 28 within the sheath 38. Preferably, the outer surface of the sheath 38 is tapered at the distal end 44.

The wire 28 is inserted into the sheath 38 such that the distal end 44 of the sheath 38 surrounds the piercing tip 36 of the wire 28. Preferably, the sheath 38 has a length greater than that sufficient for the proximal end 46 of the sheath 38 to be outside the patient's mouth when the distal end of the sheath 38 and wire 28 are intubated into the patient's small bowel. Preferably, the sheath 38 has a length which is in the range of only 10 to 20 centimeters less than the length of the wire 28. Although it is preferable for the wire to be approximately 10 to 20 centimeters larger than the sheath, thereby allowing room for manipulation of the two, it is contemplated that the wire need only be slightly longer than the sheath, to allow sufficient amount of the piercing point to emerge from the sheath distal end. Also, the wire 28 and the sheath 38 are preferably long enough to functionally extend beyond the length of the working channel of the endoscope 16. Further, the outer diameter of the needle-sheath combination should be less than, preferably much less than, the inner diameter of the endoscope working channel. For example, if the working channel of the endoscope is 9 French (3 millimeters), then it is preferable for the sheath to have an outer diameter of about 4 French (1.30 millimeters).

It is preferable to have at least one calibration mark 50 on the wire 28 to indicate the position of the proximal end 46 of the sheath 38 when the piercing tip 36 of the wire 28 is entirely within the sheath 38. Therefore, if the calibration mark 50 is visible, the piercing tip 36 is not exposed beyond the distal end 44 of the sheath 38. As the sheath is moved toward the proximal end 30 of the wire 28, the piercing tip 36 is emergent from within the sheath 38. At least one target mark 52 is included on the wire 28. The target mark 52 is preferably provided at a location toward the proximal end 30 of the wire 28 such that, when the proximal sheath end 46 is aligned with the target mark 52, the piercing tip 36 of the wire 28 is exposed at a predetermined distance from the sheath 38.

Figure 3:
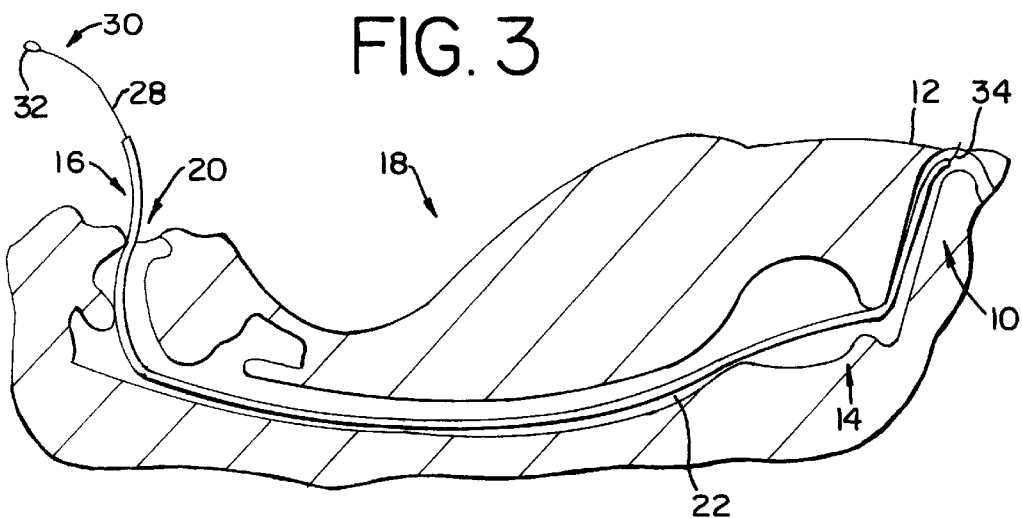
FIG. 3 is a cross-section view demonstrating manipulation of an endoscope and a probe to push the jejunum toward apposition with the abdominal wall.
Figure 4:
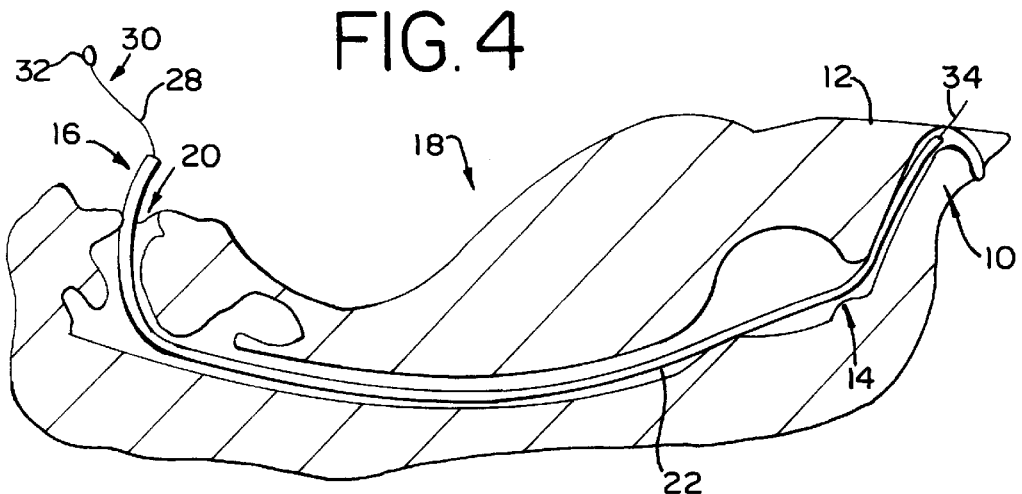
FIG. 4 is a cross-section view demonstrating the piercing of the jejunal wall and the abdominal wall with a wire of the probe.

As is best shown in FIG. 3, the wire 28 within the sheath 38 is inserted within the working channel of the endoscope 16, which is intubated into the patient's jejunum 10. Preferably, the wire and sheath combination are inserted into the working channel of the endoscope 16 prior to passing the endoscope 16 into the patient's small intestine. The endoscope 16, wire 28 and sheath 38 are manipulated such that the jejunum 10 may be in approximate apposition with the anterior abdominal wall.

In the preferred embodiment, the piercing tip 36 of the wire 28 is maintained within the sheath 38 while the jejunum is manipulated into position (such as when the sheath's proximal end 46 is aligned with the calibration mark 50 on the wire 28). Preferably, positioning the jejunum 10 is achieved by manipulation of the endoscope 16, and possibly the wire 28 and sheath 38. The manipulation of the position of the jejunum 10 is achieved by observation through the endoscope 16, and by observing the position of the distal end of the endoscope 16 and by transillumination of the abdominal wall.

Once the jejunum 10 is situated satisfactorily in proximity with the inner abdominal wall, the piercing tip 36 of the wire 28 is exposed (such as when the sheath proximal end 46 is aligned with the target mark 52). As disclosed in FIG. 4, piercing tip 36 is pierced through the wall of the jejunum 10 at the location of jejunal transillumination. Piercing tip 36 is next advanced through the abdominal wall to create a tract in the abdominal wall.

Figure 5:
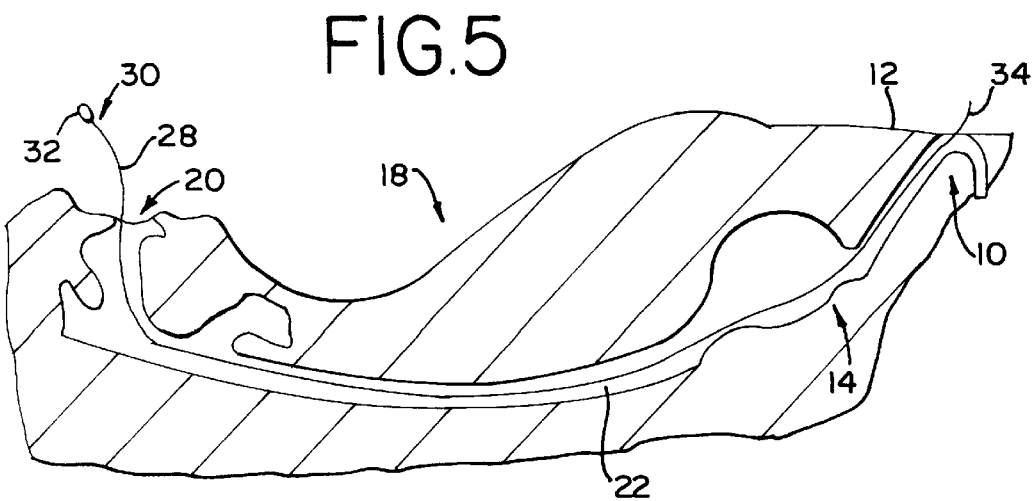
FIG. 5 is a cross-section view demonstrating the endoscope having been removed, and the probe passing in the body from the mouth through the jejunal wall and out the abdominal wall.

It is preferable to then advance the sheath over the exposed piercing tip of the wire, and to secure the sheath to the distal end 34 of the wire 28, such as with hemostats (not shown). As best shown in FIG. 5, the endoscope 16 is withdrawn from the patient's body 18. At this point in the procedure, the wire 28 passes through the patient's body 18, with the proximal end 30 of the wire 28 nearest the patient's mouth 20, and the distal end 34 of the wire 28 protruding from the jejunum 10 to the outside the patient's abdomen 54.

Figure 6:
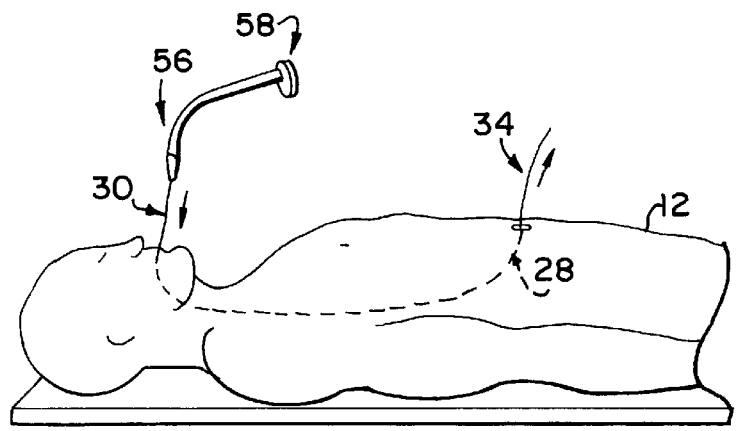
FIG. 6 is a side view demonstrating a PEG tube being pulled through the body.
Figure 7:
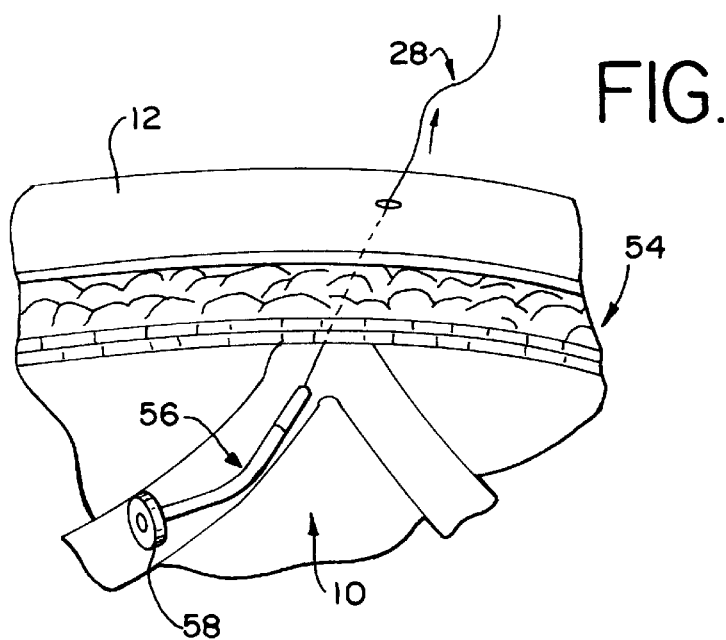
FIG. 7 is a partial cross-section view of the abdomen demonstrating a wire with a PEG tube attached being pulled from the jejunum through the abdominal wall.

As is best shown in FIG. 6, a catheter tube 56 is attached to the wire proximal end 30, preferably utilizing the loop 32. For example, the loop 32 may be hitched, or otherwise locked, to a similar loop (not shown) provided on the catheter tube 56. Once the catheter tube 56 is securely attached to the wire 28 and is lubricated, the wire 28 is pulled from the distal end 34, thereby pulling the wire 28, sheath 38, and catheter tube 56 through the mouth 20, the esophagus 22, the stomach 14, and into the jejunum 10, as shown in FIG. 7. The wire 28 is pulled further, until the catheter tube 56 extends from within the jejunum 10, through the jejunal wall and the abdominal wall, to outside the patient's body 18. It may be necessary to make a slight incision into the wall of the patient's abdominal wall 54 to allow passage of the tube.

Figure 8:
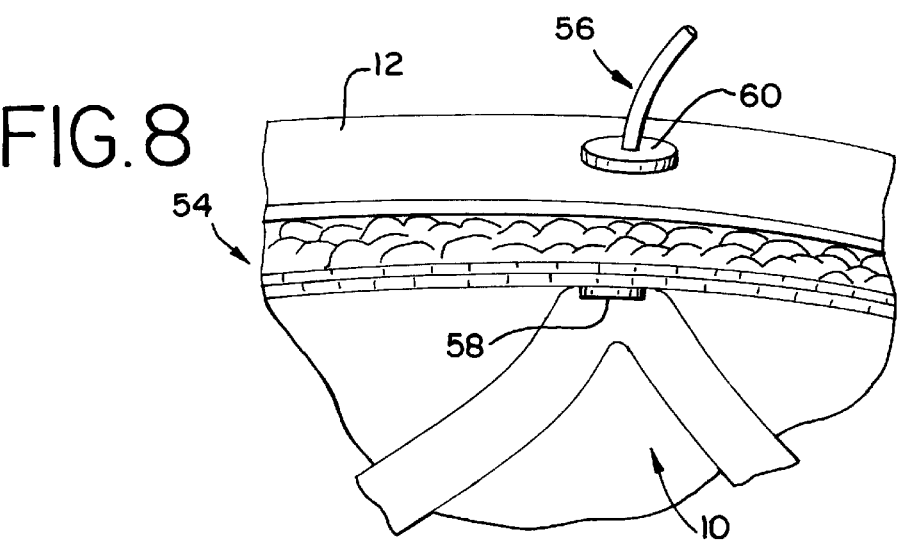
FIG. 8 is a partial cross-section view of the abdomen with a PEG tube in place.

As is best shown in FIG. 8, the catheter tube 56 preferably includes a retention member 58, such as a bumper. The retention member 58 preferably has a low profile, yet has a wide circumference for abutment against the inside of the jejunum 10, such as with a disc-shaped bumper.

Once the catheter tube 56 is in place, and the jejunum 10 is drawn as close as possible toward the abdominal wall, it is preferable to attach an external fixation device 60 to the catheter tube 56, outside the patient's body 18. The fixation device 60 abuts against the patient's skin 12 and serves to secure the catheter tube 56 in place, while also maintaining the jejunum 10 close to the abdominal wall. The catheter tube 56 may then be connected to the desired medical apparatus, such as connection of the nutrient source to feed the patient directly into the jejunum 10.

Figure 11:
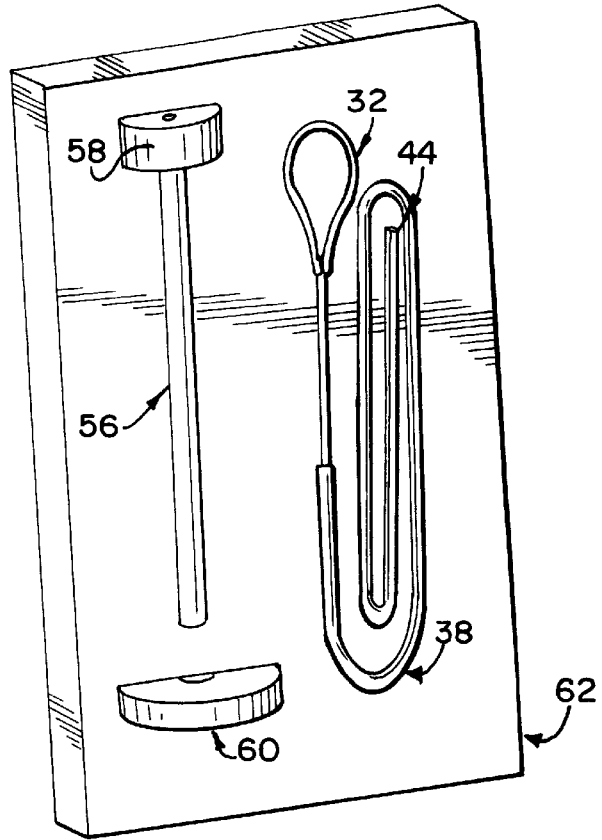

As is best shown in FIG. 11, the present invention provides a kit apparatus 62 for the procedure of intubating a direct jejunostomy tube. The kit 62 includes at least a wire 28, a sheath 38, a catheter tube 56 with a retention member 58, and a fixation device 60 for attaching to the tube 56 outside the abdomen and securing the tube 56 in place. Preferably, the wire of the kit is preloaded, i.e., inserted into the sheath. The wire 28, as is described above, includes a piercing tip 36 at one end, and a bend at the opposite end, preferably as a loop 32. The sheath 38, as is described above, includes an inner lumen 48 suitable for receiving the wire 28 within the sheath 38. Preferably, the sheath also includes a tapered outer surface of the distal end 44.

While the specific embodiments have been illustrated and described, numerous modifications come to mind without significantly departing from the spirit of the invention and the scope of protection is only limited by the scope of the accompanying claims.

I claim:

1. A kit for performing a direct percutaneous endoscopic jejunostomy in the body of a patient having an abdominal wall and having a mouth leading to an esophagus and a stomach which leads to a jejunum comprising:

a wire, having a needle piercing tip at one end and a loop at the opposite end of the wire, the loop being adapted to pass through the working channel of an endoscope;

a sheath, having an inner lumen suitable to receive said wire forming a wire/sheath combination, said wire/sheath combination being flexible and having an outer dimension adapted to pass within a working channel of an endoscope and a length greater than the length of the endoscope and being adapted to pass from a the patient's mouth through the esophagus and stomach and jejunum of the patient's body outside the patient's abdominal wall;

a catheter tube, having a tube portion and a retention member;

the retention member including a disc-shaped bumper;

a fixation device suitable for fastening to the tube portion of the catheter tube; and, a clamp suitable for clamping the wire.

2. The kit according to claim 1 wherein: the retention member of the catheter tube is a disc-shaped bumper, having an inner lumen aligned with the tube portion.

3. The kit according to claim 1, including:

sterilization swabs suitable for treating the exterior surface of the patient's abdomen.

4. The kit according to claim 1, including:

a connector suitable for joining the catheter tube to a nutrition source tube.

5. The kit according to claim 1 wherein said wire is fully received into said inner lumen of said sheath.

* * * * *